United States Patent
Groenke

Patent Number: 5,887,587
Date of Patent: Mar. 30, 1999

[54] FACIAL MASK FOR RESPIRATORY APPARATUS

[75] Inventor: Allen W. Groenke, Bloomington, Minn.

[73] Assignee: Edentec Corporation, Eden Prairie, Minn.

[21] Appl. No.: 350,647

[22] Filed: Dec. 7, 1994

[51] Int. Cl.$^6$ ........................................ A62B 7/02
[52] U.S. Cl. .................. 128/207.13; 128/206.18; 128/206.24; 128/207.11
[58] Field of Search ............... 128/204.18, 203.12, 128/200.24, 207.11, 204.28, 206.29, 205.17, 202.27, 207.13, 206.13, 206.18, 206.24

[56] References Cited

U.S. PATENT DOCUMENTS

| | | | |
|---|---|---|---|
| 2,540,567 | 2/1951 | Bennett | 128/207.11 |
| 3,009,462 | 11/1961 | Hawley | 128/204.28 |
| 4,328,797 | 5/1982 | Rollins, III et al. | 128/207.13 |
| 4,702,243 | 10/1987 | Smith | 128/204.18 |
| 5,065,756 | 11/1991 | Rapoport | 128/204.18 |
| 5,074,297 | 12/1991 | Venegas | 128/204.18 |
| 5,117,819 | 6/1992 | Servidio et al. | 128/204.18 |
| 5,222,486 | 6/1993 | Vaughn | 128/200.24 |
| 5,243,971 | 9/1993 | Sullivan et al. | 128/204.18 |
| 5,429,125 | 7/1995 | Wagner et al. | 128/204.18 |

OTHER PUBLICATIONS

Criner et al., "Efficacy of a New Full Face Mask for Noninvasive Positive Pressure Ventilation", *Chest,* vol. 6, No. 4, Oct., 1994, pp. 1109–1115.

*Primary Examiner*—John G. Weiss
*Assistant Examiner*—V. Srivastava
*Attorney, Agent, or Firm*—Nawrocki, Rooney & Sivertson P.A.

[57] ABSTRACT

A facial mask for use in medical respiratory treatments such as sleep apnea CPAP therapy. The mask includes a preferably transparent front plate to which is attached a skirt of flexible material adapted to sealingly impinge on the face of a patient. The mask is of sufficient size so that as it seals the nose from all but the desired therapeutic airflow, the sealing pressures will be felt on the forehead, the upper lip, and the malar region of the face spaced from the nose. Thus pressure on the bridge of the nose and in the maxillary region adjacent to the nose are avoided, resulting in a significant decrease in the possibility of intense pain.

11 Claims, 3 Drawing Sheets

FACIAL MASK FOR RESPIRATORY APPARATUS

BACKGROUND OF THE INVENTION

1. Field of the Invention

The present invention relates generally to sleep apnea, more specifically to apparatus for alleviating sleep apnea, and still more particularly to an improved facial mask for use with respiratory assist apparatus.

2. Description of the Prior Art

It has been known for some time that sleep apnea can be alleviated through the use of respiratory assist apparatus, such as is used in the well known continuous positive airflow pressure (CPAP) therapy. It is also well recognized that one of the primary causes for patient non-compliance with CPAP or other device therapy is significant physical discomfort cause by the facial masks such devices require.

CPAP therapy essentially requires that air pressure be provided through the patient's nostrils to assist the muscles in the throat to prevent throat blockage during sleep, thus assuaging snoring and actual interruption of breathing. A respirator machine is connected to the patient's nostrils through airflow tubing connected to a facial mask placed over the patient's nose.

Because the flow of air from the machine must be directed to the nostrils with little or no loss of pressure, the facial mask is normally sealed around the entire nose and held in place by pressure from adjustable straps that fit around the patient's head. It is this necessary sealing pressure on the mask that causes the discomfort felt by the patient.

There are at least two known causes of patient discomfort when prior art apnea therapy masks are in use: pressure facial neuralgia and vacuum sinusitis. Pressure facial neuralgia is caused by tissue being compressed against the facial bones, for example by a facial mask. Vacuum sinusitis is a painful result of a build up of pressure in the maxillary cavities located in the maxillary bones located adjacent to the nose. This build up of pressure is often associated with external pressure placed on the maxillary bones by a facial mask.

One common form of facial mask used in CPAP therapy is the generally V-shaped nose mask that is placed over the entire nose, generally reaching from the bridge of the nose to just below the nostrils. Because the potential discomforts described above are well known to those of skill in the art, this nose mask is usually provided in a variety of sizes so the patient may be fitted as accurately as possible. The mask edge is provided with a soft sealing material, generally a plastic, in an attempt to fully seal air flow around the entire nose, and the mask is held in place against movement by the weight of the tubing and patient sleep motion with a set of adjustable straps that wrap around the patient's head and apply pressure to keep the mask sealed against the facial tissue.

Another form of a respiratory treatment mask is the full face mask described in an article entitled "Efficacy of a New Full Face Mask for Noninvasive Positive Pressure Ventilation," by Criner et al, CHEST, Vol. 106, pp. 1109–15, October, 1994. This TFM (total face mask) device is preferred for the NPPV therapy discussed by the authors, and is intended to reduce patients' complaints about, for example, air leakage, facial discomfort and claustrophobia. This TFM device is not suitable for most sleep apnea therapy, in particular CPAP therapy, because it is usually preferred that the mouth be uncovered.

Other forms of masks have been designed for use in apnea therapy, such as the "pillows" which comprise a pair of soft plastic tubes adapted to fit within the nostrils. This mask, though preferred over the nose mask by some patients, faces the problems of pressure caused by the connection of the air tubing to the pillow mask and the necessary holding of the tubing and mask from sufficient movement to extricate a pillow from a nostril, as well as an added problem with increased drying airflow directly within the nostrils.

Though the prior art masks have been made of a design and materials intended to ease patient discomfort, the disadvantage of causing pressure on the facial tissue and bones still exists. Some patients simply cannot accept the pain that comes with the desired therapy.

SUMMARY OF THE INVENTION

The present invention overcomes the disadvantages found in the prior art by providing a facial mask of sufficient size to rest primarily on the forehead and the upper lip, and on the malar area of the patient's face. The improved mask preferably comprises a generally oval-shaped front plate to which is attached a skirt made of a material such that the edges of the skirt easily seal against the face to prevent airflow loss from the chamber formed between the mask and the patient's face. The apparatus of this invention carries adjustable straps adapted to fit around the patient's head, as well as an air tube connection port. The front plate preferably has at least a transparent portion. The use of the forehead and the malar area spaced from the nose to receive much of the sealing pressure significantly alleviates pressure facial neuralgia and vacuum sinusitis.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
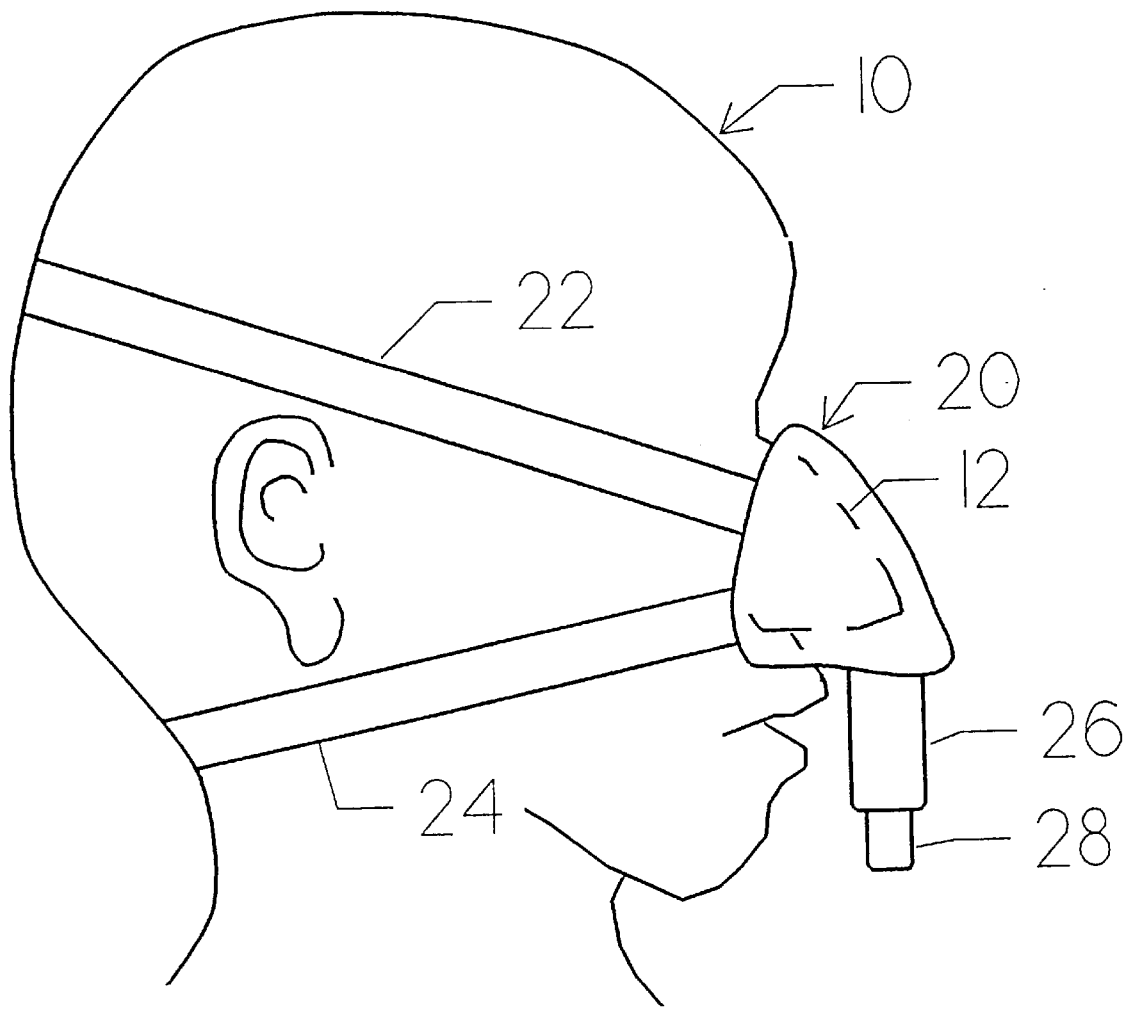
FIG. 1 is a side view representative of a human head and showing a well known prior art facial mask for use with respiratory devices.

FIG. 1 discloses a human head 10 having a nose 12. A prior art facial mask 20 is shown fitting over nose 12. Mask 20 is held in place by pressure from a pair of adjustable, flexible straps 22 and 24. A swivel air flow connector 26 is connected to mask 20, and carries a tube connector 28 adapted to receive an air flow tube from a respiratory aide device such as a CPAP device.

Mask 20 is of a material sufficiently pliant to allow it to seal when pressure-biased against a portion of the face. In the case of prior art mask 20, the sealing takes place across the bridge of nose 12, along the upper lip of head 10, and along the facial tissue adjacent to each side of nose 12.

Although broadly in use, the prior art mask 20 has some significant disadvantages because of its manner of sealing with the face of head 10. In particular, the necessary sealing pressure on the tissue across the bridge of nose 12 and the tissue along each side of nose 12 will make the tissue compress against the facial bones and may cause highly painful pressure facial neuralgia. Further, this same pressure along the sides of the nose may cause extreme pain due to vacuum sinusitis resulting from a pressure build up inside the maxillary cavities. These undesirable high pain levels may cause effected patients to elect to discontinue the otherwise valuable respiratory therapy.

Figure 2:
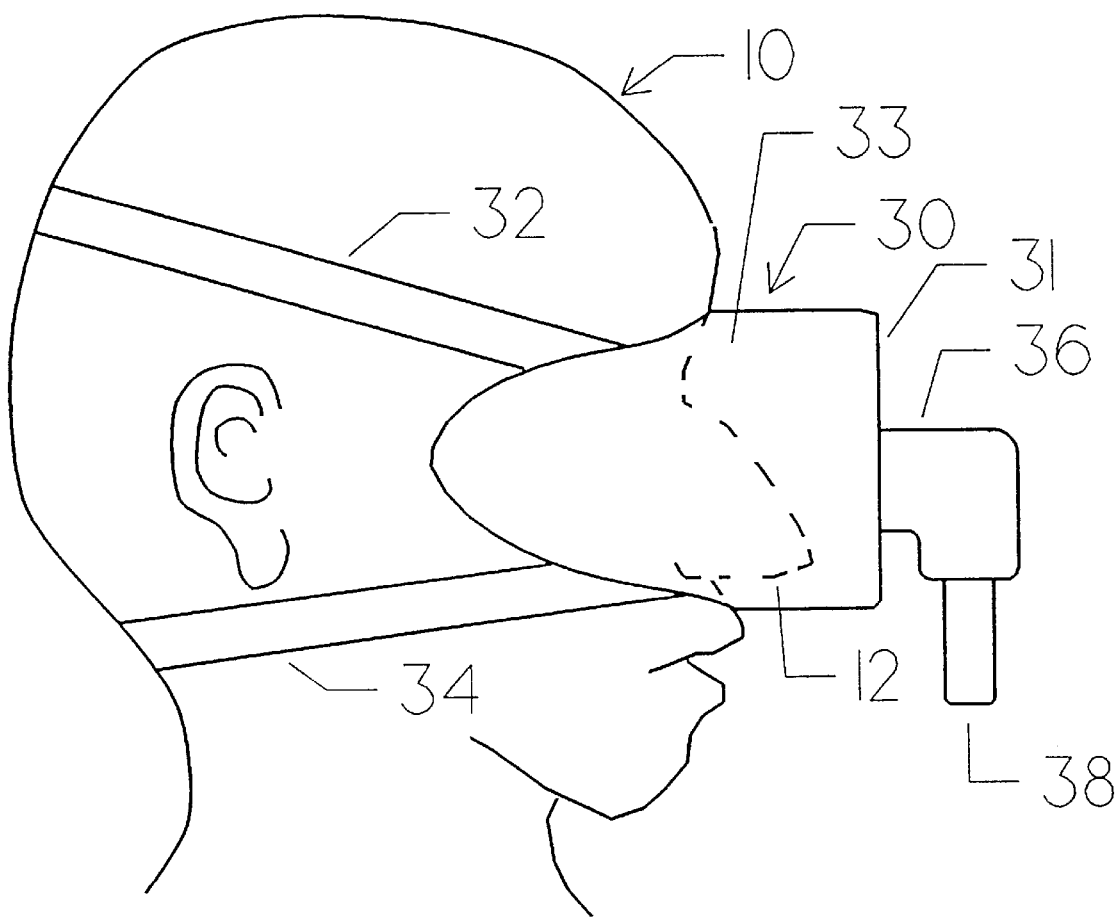
FIG. 2 is a side view similar to FIG. 1 in which the prior art mask is replaced with the mask of the present invention.
Figure 3:
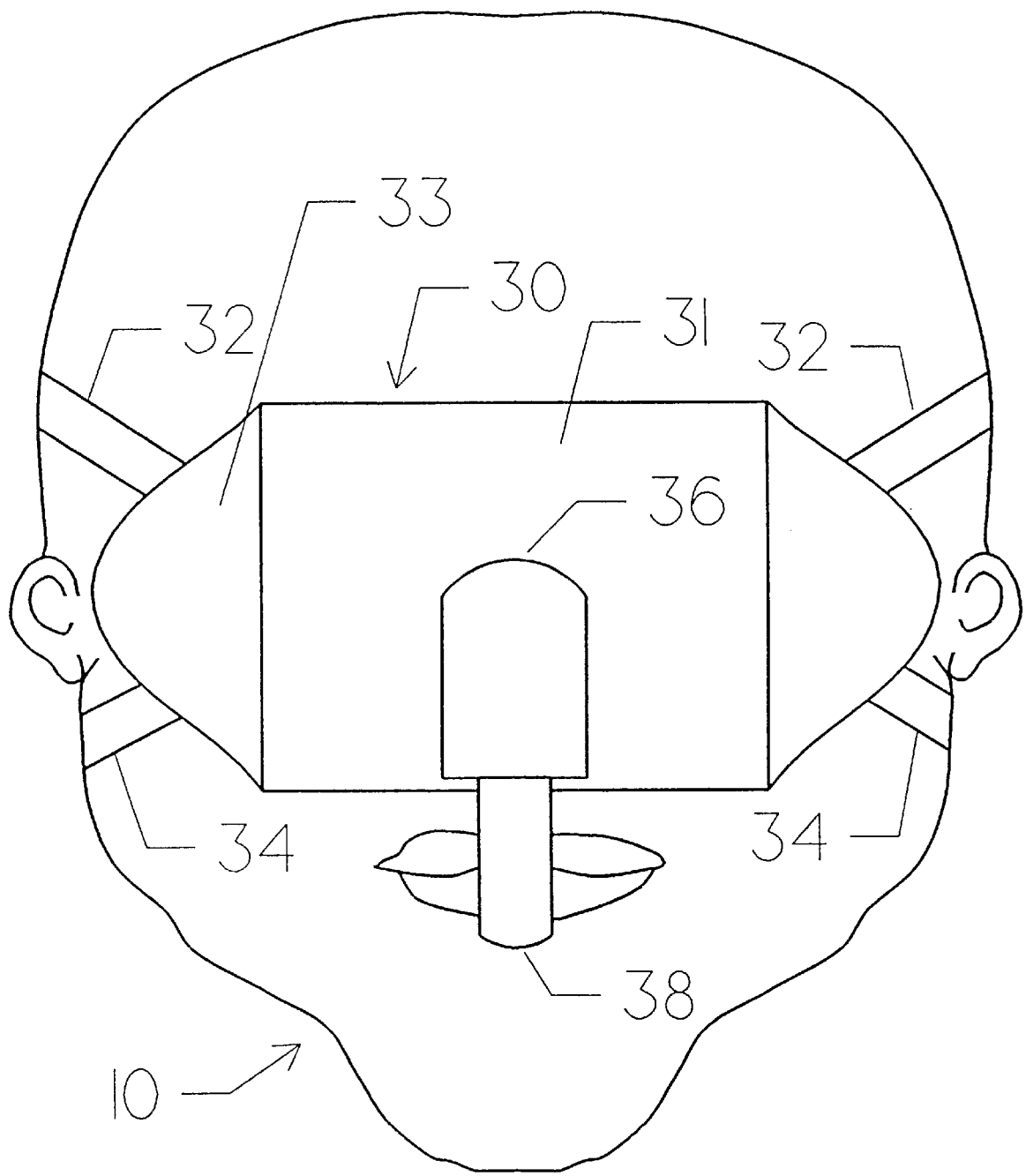
FIG. 3 is a frontal view of the head and mask of FIG. 2.

To overcome the disadvantages of the prior art mask of FIG. 1, an improved facial mask 30 is shown in FIGS. 2 and 3. Mask 30 has a front plate 31 which is preferably generally ovate or generally rectangular. A pliable or flexible skirt 33 has its proximal edges sealingly connected to plate 31. Mask 30 is of a size selected so that when placed over nose 12 of head 10, the distal edges of skirt 33 will impinge on the face of head 10 along the forehead, the upper lip, and in the malar area well spaced from nose 12, to form a sealed chamber.

Mask 30 is shown in FIGS. 2 and 3 as carrying a pair of preferably adjustable and flexible straps 32 and 34 that fit around head 10 to apply pressure to and hold in place mask 30. In the preferred embodiment at least the distal edges of skirt 33 are made of a material sufficiently pliant to seal against air flow loss at the sites of impingement of mask 30 on the face, with the sealing pressure provided by the adjustment of straps 32 and 34.

Also shown in FIGS. 2 and 3 is a swivel airflow connector 36 which is mounted to a port through plate 31 of mask 30 to allow for airflow into the chamber formed between the patient's face and mask 30 by the attachment of mask 30 to head 10 in the manner shown and described above. Connector 36 carries an airflow tube connector 38.

In the preferred embodiment of FIGS. 2 and 3 all or a portion of plate 31 could be made to have any degree of transparency so that the patient could, for example, see a clock without interrupting the therapeutic airflow.

Having thus described the preferred embodiments of the present invention, those of skill in the art will readily appreciate the other useful embodiments within the scope of the claims hereto attached.

I claim:

1. A method of providing a continuously positive air pressure to a patient to maintain an open respiratory airway within the patient, comprising the steps of:

providing a face mask including a front plate; a skirt mounted to and extending generally obtusely from said plate; said skirt having a proximal edge sealingly connected around the perimeter of said front plate; said skirt having distal edges for making sealing engagement with the face of a patient along the forehead and upper lip of the patient, and in the malar area of the patient's face significantly spaced from the patient's nose; and the mask including an air passage for allowing a flow of air into the chamber formed by the sealing engagement of the mask with the patient's face;

placing the mask in sealing engagement with the patient's face while leaving the patient's mouth exposed to ambient air pressure; and coupling to the mask air flow tubing means for delivering a continuously positive air pressure to the chamber.

2. The method of claim 1 in which at least said distal edges of said skirt comprise a flexible material.

3. The method of claim 1 in which said skirt comprises a flexible material.

4. The method of claim 1 including adjustable straps connected to said skirt for holding said distal edges of said skirt in sealing relation with the face of the patient.

5. The method of claim 1 in which at least a portion of said front plate comprises a transparent material.

6. The method of claim 1 in which said air passage comprises a pneumatic port extending through said front plate for providing a flow of air to said chamber.

7. The method of claim 6 including adjustable straps connected to said skirt for holding said distal edges of said skirt in sealing relation with the face of the patient.

8. The method of claim 6 in which at least a portion of said front plate comprises a transparent material.

9. The method of claim 6 including swivel connection means for pivotably connecting the air flow tubing means to said port.

10. The method of claim 9 including adjustable straps connected to said skirt for holding said distal edges of said skirt in sealing relation with the face of the patient.

11. The method of claim 9 in which at least a portion of said plate comprises a transparent material.

\* \* \* \* \*